(12) United States Patent
Dufaud et al.

(10) Patent No.: US 6,171,475 B1
(45) Date of Patent: Jan. 9, 2001

(54) PROCESS FOR CONTROLLED DEGRADATION OF HYDROCARBON POLYMERS

(75) Inventors: Véronique Dufaud; Jean-Marie Basset, both of Villeurbanne (FR)

(73) Assignee: CPE-Lyon-FCR, Villeurbanne Cedex (FR)

( * ) Notice: Under 35 U.S.C. 154(b), the term of this patent shall be extended for 0 days.

(21) Appl. No.: 09/005,444

(22) Filed: Jan. 12, 1998

Related U.S. Application Data (63) Continuation-in-part of application No. PCT/FR96/01092, filed on Jul. 12, 1996.

(30) Foreign Application Priority Data

Jul. 13, 1995 (FR) .................................................. 95 08552

(51) Int. Cl.[7] .................................................. C10G 47/12
(52) U.S. Cl. .................................. 208/111.1; 208/111.01; 208/111.05; 208/111.2; 208/111.25; 208/111.3; 208/108; 208/109; 208/111.15; 585/241
(58) Field of Search ....................... 585/241; 208/111.01, 208/111.1–111.3, 108, 109

(56) References Cited

U.S. PATENT DOCUMENTS

| | | | |
|---|---|---|---|
| 3,917,737 | * 11/1975 | Yoo | 260/683.9 |
| 4,108,730 | * 8/1978 | Chen et al. | 201/2.5 |
| 4,165,276 | * 8/1979 | Antos | 208/139 |
| 4,513,098 | * 4/1985 | Tsao | 502/216 |
| 5,162,446 | 11/1992 | Gibler et al. | 525/338 |

\* cited by examiner

Primary Examiner—Walter D. Griffin
Assistant Examiner—Nadine Preisch
(74) Attorney, Agent, or Firm—Young & Thompson (57) ABSTRACT

A method for converting a polymer or oligomer derived from an ethylenically unsaturated monomer into alkanes or into a hydrocarbon fraction or a lower oligomer fraction by controlled hydrocracking, wherein the polymer or oligomer is exposed to a catalyst based on a metal hydride or an organometallic complex supported on a mineral carrier, the complex having at least one hydrocarbon ligand and optionally at least one hydride ligand, and the resulting mixture is reacted with hydrogen to cause catalytic hydrocracking of the polymer or oligomer. The polymer or oligomer is broken down into reclaimable products with a lower molecular weight for use, e.g., in the field of polymers, particularly controlled molecular weight polymers, fuels or lubricants.

23 Claims, 7 Drawing Sheets

PROCESS FOR CONTROLLED DEGRADATION OF HYDROCARBON POLYMERS

This application is a continuation-in-part of international application PCT/FR96/01092 filed Jul. 12, 1996, which designed the United States.

FIELD OF THE INVENTION

The present invention relates to a novel catalytic process leading to the controlled degradation of heavy hydrocarbons under the effect of hydrogen into upgradeable products such as methane and lower alkanes, higher alkanes or any type of hydrocarbon, or oligomers or polymers of the lower variety covering a very wide range of molecular weights.

BACKGROUND OF THE INVENTION

Heavy hydrocarbons which may be degraded by this novel process are in particular waxes. Such waxes are hydrocarbons in $C_{12}$ to $C_{50}$ which generally are saturated. However, they can be sometimes unsaturated. They can be derived from processes of synthesis like Fischer-Tropsch. In fact, their structure is very similar to the structure of oligomers based on low molecular weight polyethylene.

Polymers which may be degraded by this novel process are polymers having chains with carbon—carbon bonding, for example polyethylene, polypropylene or polystyrene.

Among the fields of application of the invention, mention may be made of environmental protection or the polymer production industry, in particular appertaining to polymers with controlled molecular mass, petrochemical products, fuels (hydrocarbon fractions), lubricants or alternatively energy.

The invention is in particular advantageous in the field of fuel for obtaining hydrocarbon fractions like diesel, which is constituted of hydrocarbons in $C_{12}$ to $C_{20}$, from waxes derived from Fischer-Tropsh's synthesis. As these waxes are solid at room temperature, their conversion needs very high temperatures with conventional catalysts. According to the present invention this conversion can be achieved by reacting waxes with hydrogen in less severe conditions.

The invention can also find applications in the food packaging industry, or that appertaining to any other type of packaging where the polymer waste produced during manufacture cannot be reused.

Heightened environmental protection requires the implementation of reliable new techniques for processing the polymer waste commonly referred to as plastics. Among the various methods envisaged for the reuse or disposal of used polymers, energy and/or chemical recycling may afford satisfactory solutions complementary to material recycling.

Among the solutions relating to plastics waste, incineration with or without energy recovery constitutes one possible way, but the temperatures needed for this type of processing are very high, of the order of 400 to 700° C. However, this type of process can only lead to energy recovery from polymers, and has the drawback of being unecological because it would increase the greenhouse effect.

Chemical recycling is starting to attract great interest. This technique consists in chemically decomposing the macromolecules with a view to obtaining molecules which have low molecular masses and can be reused with regard to their physical or chemical or energy (fuel) properties. In general, catalytic degradation (cracking or hydrocracking) of polyolefins makes it possible to improve the selectivity of this type of reaction in comparison with purely chemical and thermal processes, and consequently to obtain directly hydrocarbon fractions which are easier to upgrade. The catalysts for cracking and hydrocracking polypropylene or polyethylene are generally silicas, silica/aluminas, zeolites or catalysts based on cobalt and molybdenum which operate at elevated temperature, typically between 200 and 600° C. and most often towards 400° C. and under high hydrogen pressure. These techniques are described, in particular, by BELTRAME et al., in Polymer degradation and stability, 26, (1989) 29–220., HIROTA et al., in Makromol. Chem. Macromol. Symp. 57, 161–173 (1992), Y. ISHIRA et al., Fuel, 69, 978, (1990), I. KORFF et al., in Erdol Erdgas 105, (1989) 223.

SUMMARY OF THE INVENTION

The object of the present invention is to provide a novel catalytic process for hydrocracking waxes or polymers of the polyolefin type, which can be employed in less severe conditions than the processes known hitherto, with the purpose of using simplified equipment to easily and efficiently produce upgradeable products with a variety of applications according to their molecular mass.

The present invention thus relates to a process for the conversion of a wax or a polymer or an oligomer, said oligomer or said polymer deriving from an ethylenically unsaturated monomer, into alkanes or a hydrocarbon fraction or an oligomer fraction of the lower variety by controlled hydrocracking, characterized in that it comprises the steps consisting in:

bringing the said wax or polymer or oligomer into the presence of a catalyst based on a metal hydride or an organometallic complex supported on an inorganic support, the said complex including at least one hydrocarbon ligand, and optionally at least one hydride ligand, then reacting this mixture with hydrogen, thus catalytically hydrocracking the said polymer or oligomer.

According to the present invention, the expression "alkanes or a hydrocarbon fraction or an oligomer fraction of the lower variety" means hydrocarbon compounds whose chain includes a number of carbon atoms lower than the number of carbon atoms in the initial polymer or oligomer or wax.

Using a very high-performance catalyst, it is possible according to the invention to hydrocrack polyolefins such as polyethylene, polypropylene, polystyrene or polyisoprene, in temperature and pressure conditions which are remarkably low compared to those customarily required in the prior art for reactions employing macromolecular solid material, in which low conditions conventional hydrocracking catalysts (silica, silica/alumina, zeolites) are inactive. The process can thus be employed with simplified apparatus in improved safety conditions. However, the originality of the present invention resides primarily in the great versatility of the operating conditions of the process, and these will be described below, making it possible to set the selectivity appertaining to the formation of certain degradation products, that is to say to carry out controlled degradation of the macromolecules.

As regard waxes, they are saturated or optionally olefinic hydrocarbons in $C_{12}$ to $C_{50}$. They can be derived from Fischer-Tropsch's synthesis.

As regards polymers, the present invention permits, in particular, controlled degradation of polyolefins in order to give polymers with specific properties that are more beneficial owing to the molecular mass modification. This controlled degradation can also be carried out during the polymerization process, but more generally after polymerization, that is to say when forming the polymer.

More generally, the polymers that can be degraded according to the invention may derive from monomers having a single polycondensable ethylenic unsaturation, either of the olefinic type, such as ethylene, propylene, isobutylene, methylpentene, hexene, or of the aromatic alkenyl type, such as styrene, the vinylpyridines or vinylnaphthalenes, and/or monomers having a plurality of polycondensable ethylenic unsaturations, such as butadiene, isoprene, piperylene, methylpentadiene, phenylbutadiene, dimethylhexadienes, dimethyloctadienes.

The process according to the invention applies more advantageously to waxes or polymers whose hydrocarbon skeleton is a saturated polyolefin, optionally substituted, which derive from one or more monomers including a single ethylenic unsaturation.

These polymers, such as polyethylene or polypropylene, are known for their exemplary thermal and chemical stability. It is this extraordinary chemical stability which has made them successful. Unfortunately, it is this thermal and chemical stability which makes it particularly difficult to solve the ecological problem posed by the waste produced by these polymers. The invention described here gives particularly spectacular results as regards the conditions for hydrocracking saturated polyolefins, in particular polypropylene and polyethylene.

The invention also applies to polymers whose hydrocarbon skeleton, optionally substituted, includes unsaturations, and which originate from a monomer including a plurality of ethylenic unsaturations. These unsaturated polymers are in general easier to degrade than the former polymers because their chain is highly susceptible to cleavage at the unsaturations. The process according to the invention is, however, highly advantageous in terms of controlling the degradation since it also makes it possible to degrade the saturated parts of the polymer chain in order to reduce it to small units.

The invention also applies advantageously to copolymers whose hydrocarbon skeleton is unsaturated and which derive from at least one monomer having one ethylenic unsaturation and at least one monomer having a plurality of ethylenic unsaturations, as well as to mixtures of saturated and unsaturated polymers derived from monomers of this type.

The catalysts relevant to the present invention are catalysts based on metal hydrides or on complexes, in particular hydride complexes, of metals, preferably transition metals, supported on an inorganic support.

The most beneficial compounds are those of oxyphilic transition metals, in particular metals in groups IIIb, IVb, Vb and VIb of the Periodic Table, including lanthanides and actinides. The most beneficial hydrides are, for example, the hydrides of scandium, yttrium, lanthanum, zirconium, hafnium, titanium, tantalum, vanadium, niobium, chromium, molybdenum, tungsten. Among the lanthanides and actinides, mention may, in particular, be made of cerium, lanthanum, neodymium, etc.

During the present description, the term metal hydride means an inorganic compound in which the metal is bound to at least one hydrogen atom in hydride form, and optionally other ligands such as a halide. In the supported form of the hydride, the metal may also be bound to one or more functional groups of the surface of the support.

The term organometallic complex is intended to mean any co-ordination complex in which the metal is bound to at least one carbon atom. According to the invention, the metal is bound to at least one saturated or unsaturated carbon-based ligand, preferably $C_1$ to $C_{20}$, bound to the metal by at least one carbon atom. The ligands may be a σ ligands, such as alkyl, aryl, carbonyl, acyl, or π ligands such as carbene, arene, carbine, diene, in particular cyclopentadienyl, optionally substituted. The number of ligands depends on the oxidation state of the metal, which is typically from 2 to 7. It is preferable for at least one hydrocarbon ligand to be of the σ type, preferably an alkyl or aryl group. Mention may, in particular, be made of the methyl, ethyl, propyl, isobutyl and neopentyl groups. It is highly advantageous for all the ligands to be of the σ type.

The organometallic complexes that can be used according to the invention may optionally furthermore include at least one hydride ligand.

The other ligand or ligands, the number of which depends on the oxidation state of the metal, may be of a variety of types, in particular halide or oxo.

In the supported form of these organometallic complexes, the metal may also be bound to one or more functional groups of the surface of the support.

The compound of the metal may therefore include zero, one or more hydrogen atoms in hydride form in its structure when it is introduced into the reaction medium. During the catalytic cycle, the metal transfers hydrogen atoms from the $H_2$ molecules to the polymer chains, causing the carbon—carbon bonds to break. When the metal is introduced in the form of a hydrocarbon complex, in particular alkyl, a hydride complex capable of performing this transfer is assumed to be formed in situ.

Although the exact cause of the particular reactivity of these catalysts with respect to hydrocracking the polymers has not truly been defined, it would seem that the support on which the metal compound is fixed interacts with the co-ordination sphere of the metal to form a highly reactive structure.

The inorganic support may be selected from all the supports conventionally used to receive a hydrogenation catalyst, in particular metal oxides or metal chlorides, or metal sulphides such as molybdenum sulphide or tungsten sulphide.

The supports used in the present invention are preferably divided solids comprising a metal oxide or a mixture of metal oxides such as, for example, silica/alumina, silica, alumina, zeolites, mesoporous oxides, natural clays, niobium oxide, without this list implying any limitation. A preferred one of the supports is silica/alumina.

The supports based on metal oxide have the advantage that they have oxygen atoms at their surface which can form part of the co-ordination sphere of an oxophilic transition metal within the compound constituting the catalyst. The liganding of the metal by surface oxygens gives the transition metal compound greater stability while providing a strong supportmetal bond.

The supported organometallic complexes that can be used according to the invention may be prepared by grafting an organometallic complex of formula $MR_n$, where M represents the metal, R a hydrocarbon ligand as defined above and n a non-zero integer depending on the valency of M.

The supported hydride complexes or hydrides that can be used according to the invention may be produced by (i) grafting a metal compound, and preferably an organometallic complex, onto the inorganic support by reacting the support with the said compound, followed (ii) by a treatment under hydrogen of the product of step (i), intended to convert the metal or organometallic compound into the hydride of the said metal. As regards the metal or organometallic compounds, all compounds capable of being reduced in the presence of hydrogen with the formation of a hydride can be used. They preferably satisfy formula (1)

$$MH_xR_y \quad (1)$$

where M is the metal,
H is a hydride ion,
x is an integer that may be zero,
R is a hydrocarbon ligand, and
y is a non-zero integer.

If y is greater than 1, the ligands R may be identical or different.

x may be zero, the grafted compound then being an organometallic compound containing no hydride, or x may be equal to at least 1, the grafted compound then already including at least one hydride ion.

The ligand R may be any carbon-based ligand capable of forming a compound or an organometallic complex with the transition metal M.

The carbon-based chain of R advantageously includes from 1 to 20 carbon atoms.

R may be selected, in particular, from the following ligands: alkyl, carbene, carbyne, carbonyl, diene which is optionally substituted, aryl, acyl and arene.

Preferably, at least one of the ligands R is a ligand of the σ type, advantageously an alkyl or aryl group.

When M is a metal from groups IIIb, including the lanthanides and the actinides, and IVb, for example zirconium, R is advantageously selected from the alkyl and aryl groups.

When M is a transition metal other than those above, R may have other meanings. Mention may, for example, be made of alkyl/carbene/metal complexes.

The values of x and y depend on the oxidation state of the metal in the compound which it is desired to employ. In general, the metal is in a high oxidation state, but it may in other cases have a low oxidation state.

Alternatively, the complex may already contain at least one oxygen atom and be a complex of the oxo type which, in particular, satisfies formula (2)

$$M(O)_nH_pR_q \quad (2)$$

or of the alkoxy type which, in particular, satisfies formula (3)

$$M(OR')_nH_pR_q$$

where R and H have the same meaning as before,
n and q are non-zero integers, and
p is an integer that may be zero.
R' is an alkyl group, preferably $C_1$–$C_{10}$.

Complexes of this type can be formed with metals such as vanadium, niobium or tantalum, and for example satisfy the formula $MOR_3$.

It will be noted that, when the catalyst is introduced into the reaction medium in hydrocarbon complex form, step (ii) described above takes place when the polymer/catalyst mixture is reacted with hydrogen.

When the inorganic support which is used is a metal oxide, the treatment under hydrogen of a transition metal compound, once grafted, causes the oxyphilic metal to accommodate a large number of oxygen atoms from the surface, leading to a simple coordination sphere in which the metal is bound both to one or more surface oxygens and to one or more hydrogen atoms in hydride form. The metal is then bound covalently and very strongly to the surface and cannot be encountered in the reaction products. By way of example, it has been found that the zirconium monohydride bound to the surface of silica was bound to 3 oxygen atoms of the silica with a distance of 1.94 angstroms and to a fourth oxygen atom 2.6 angstroms away.

For example, a preferred one of the complexes, zirconium tetraneopentyl ($ZrNp_4$) will react with the surface of a silica/alumina or of a silica according to two possible mechanisms:

If the silica/alumina or the silica are pretreated between 200 and 500° C. before the grafting, a surface complex is obtained which satisfies the formula ($\equiv$Si—O)$_\alpha$$ZrNp_\beta$. It is this surface complex which, after treatment under hydrogen, will lead to the active catalyst for the present invention.

If the silica/alumina or the silica are pretreated to in excess of 600° C. before the grafting, a surface complex is obtained which satisfies the formula ($\equiv$Si—O)$_\alpha$$ZrNp_\beta$, $\equiv$Si—Np. It is this complex which, treated under hydrogen, will also lead to an active catalyst for the present invention.

The treatment (ii) under hydrogen is preferably carried out at a temperature of from 50 to 250° C.

The quantity of hydrogen which is used depends on the ease of reduction of the grafted compound. The hydrogen pressure in this step is advantageously about $10^5$ Pa.

Among the inorganic supports which can stabilize the catalyst in hydride form, introduced as such or formed in situ, mention may be made of any traditional oxide support, for example silica/alumina, silica, alumina, zeolites, titanium oxide, niobium oxide, magnesium oxide, supports of the metal sulphide type, in particular the sulphides of molybdenum or of tungsten, sulphated aluminas, sulphated oxides. The type of support can have an effect on the selectivity of the catalytic hydrocracking of the polymers according to the invention and contribute to determining the distribution of the products which it is desired to obtain. In certain cases, the preferred support is silica/alumina. However, silica or other oxides also lead to active catalysts, and the list is not intended to imply any limitation.

The process according to the invention makes it possible to degrade, by hydrocracking, condensation products derived from an ethylenically unsaturated monomer which have a relatively high molecular mass.

It provides remarkably effective results for macromolecules, also referred to as condensation products, of the polymer or oligomer type having a carbon-based chain comprising at least 10 carbon atoms.

The polymers which are treated may be of any type, syndiotactic, isotactic, atactic, of low or high molecular mass, and elastomeric or non-elastomeric.

In the case of polyethylene, low or high density polyethylene, of low or high molecular mass, can equally well be treated.

One of the particular features of the present invention is that it applies to macromolecules of the polymer or oligomer type whose physical properties are radically different from those of the molecules. In general, in the conventional process for hydrocracking oil fractions, molecules of alkanes or of olefins which have been converted into gas at high temperature are catalytically cleaved.

In the case of the present invention, which relates to macromolecules or polymers, the physical properties are very different and gas molecules are not encountered in the starting product. On the contrary, the polymer which is to be degraded is either solid, molten or in suspension.

The process according to the invention makes it possible to lower the temperature and hydrogen pressure conditions in comparison with the conditions of catalytic processes currently applied to macro-molecules, to levels which are less demanding in terms of apparatus and are less likely to degrade the catalyst.

The catalytic hydrocracking may advantageously take place at a temperature of from 25 to 300° C. Lowering the reaction temperature by at least 100° C. in comparison with usual processes represents a considerable saving in the energy budget of the process.

Similarly, the catalytic hydrocracking is advantageously carried out under a hydrogen pressure of from $10^3$ to $5.10^7$ Pa. The process of the invention is particularly beneficial because the polymer can be degraded under relatively low hydrogen pressure. However, if need be, a specialist may decide to work under relatively high hydrogen pressure while obtaining results which are just as beneficial.

As required, the catalytic hydrocracking may last a long or short time, and its duration may in particular be from 30 min to 150 h.

According to his requirements, a specialist will be able to alter these operating parameters, and in particular the nature of the catalyst, in these advantageous ranges or even below or above the advantageous limits which have been indicated, in order to set a particular selectivity for the reaction.

It is thus not possible to indicate absolutely preferred operating conditions. The advantage of the process of the invention is that it is entirely adaptable according to the polymer to be degraded and the desired product as upgradeable degradation residue.

When the polymer is brought into the presence of the catalyst in the desired temperature and hydrogen pressure conditions, more or less rapid degradation of the polymer is observed into oligomers and hydrocarbons of the alkane type, ranging from methane to alkanes with high molecular weight. An increasing conversion ratio will lead to the increased formation of light alkanes, the final products generally being methane, ethane and light alkanes. However, the reaction conditions may be selected so as to make it possible to obtain oligomers or hydrocarbon fractions which are particularly beneficial, for example diesel fractions, petroleum fractions, fuel fractions for motor vehicles or for jet aircraft, or alpha olefins used in the field of detergents.

The conditions in which the reaction is employed are particularly versatile and therefore beneficial and outstanding since:

the reaction can be carried out in a solvent in which the polymer may be suspended. The most beneficial solvents are cyclic alkanes such as decalin or cyclopentane, or any other inert solvent, including fluorinated solvents;

or alternatively the reaction can be employed using a solid/solid system, that is to say the catalyst, which is a solid, can be brought into contact with the polymer, which is a solid, and the reaction takes place at the solid/solid interface, the polymer preferably being in fused form, but without this being necessary.

The reaction can also apply to a mixture of polymers, for example in the simultaneous presence of polypropylene and polyethylene, or polyethylene, polypropylene and polystyrene in the reactor, this being particularly beneficial for ecological reasons in the case of the one-off reprocessing of complex waste.

The operating protocol is simple:

in batch production, the polymer to be degraded can be introduced into a batch-type reactor containing the catalyst based on metal hydride under an inert atmosphere, preferably anhydrous. A quantity of hydrogen is then introduced into the reactor and the temperature is adjusted to the desired value;

alternatively, the reaction may be carried out in batch mode in a solvent of the cyclic alkane type, such as decalin or cyclopentane. In this case, the reaction rate is slower but it is possible to have better control over the kinetics of the reaction and therefore the products which it is desired to obtain;

alternatively, the reaction can be carried out under a dynamic regime in an appropriate reactor and the catalyst, the hydrogen gas and the polymer can be sent continuously into the reactor;

alternatively, the polymer, in suspension in a solvent, can be sent onto the catalyst bed through which an appropriate partial pressure of hydrogen is passed, making it possible to obtain the product or the reaction product fraction which are desired;

alternatively, the polymer may be modified as it is shaped, for example in an extruder, and it is during this shaping that the modification takes place by simultaneous introduction of the catalyst, the polymer and hydrogen via suitable means for introducing catalyst, polymer and hydrogen.

As a variant, the process of the invention can be employed during the actual formation of the polymer or oligomer, the catalytic hydrocracking being carried out in the actual reactor for polycondensation of the monomer.

BRIEF DISCRIPTION OF THE DRAWINGS

The present invention, and in particular the versatility and the manifold benefits of the process of the invention, will now be illustrated by the following examples which refer to the appended drawings, in which.

DETAILED DESCRIPTION OF THE INVENTION

PREPARATION EXAMPLE A

This example illustrates the preparation of a catalyst of the zirconium hydride complex type supported on silica/alumina.

Flow of oxygen at 500° C. for 10 hours, 5 grams of silica/alumina (specific surface=380 m$^2$/g) containing 25% of aluminium were introduced into a glass reactor and treated under vacuum at 500° C. overnight. After this treatment, 617 mg of ZrNp$_4$ (Np=neopentyl) to be grafted onto the inorganic support were sublimed in the reactor in such a way that the silica/alumina had a zirconium content of 3%. After evacuation to remove any of the complex which may not have reacted, the reactor was put under a hydrogen pressure of $10^5$ Pa overnight at 150° C. During this process, the formation of surface hydride takes place, which leads in infrared spectroscopy to the appearance of v(Zr—H) bands at about 1642 $cm^{-1}$. Simultaneously, the appearance of v(Si—H) bands lying towards 2262 and 2198 $cm^{-1}$ is observed in infrared spectroscopy. The simultaneous appearance of the Zr—H and Si—H bands is proof of the synthesis of the correct catalyst in the context of the invention. The presence of Si—H bands indicates that the silica/alumina lattice has been deeply modified as a result of the grafting, and especially of the reduction of the grafted complex. We will refer below to this catalyst as catalyst A.

PREPARATION EXAMPLE B

This example illustrates the preparation of a catalyst of the zirconium hydride complex type supported on silica.

In a glass reactor, 5 grams of silica (specific surface=200 $m^2/g$) were treated under vacuum at 500° C. overnight. After this treatment, 617 mg of $ZrNp_4$ to be grafted onto the inorganic support were sublimed in the reactor in such a way that the silica had a zirconium content of 3%. After evacuation to remove any of the complex which may not have reacted, the reactor was put under a hydrogen pressure of $10^5$ Pa overnight at 150° C. During this process, the formation of surface hydride takes place, which leads in infrared spectroscopy to the appearance of v(Zr—H) bands at about 1649 $cm^{-1}$. Simultaneously, the appearance of v(Si—H) bands lying towards 2253 and 2191 $cm^{-1}$ is observed in infrared spectroscopy. The appearance of the Zr—H and Si—H bands is proof of the synthesis of the correct catalyst in the context of the invention. The presence of Si—H bands indicates that the silica lattice has been deeply modified as a result of the grafting, and especially of the reduction of the grafted complex. We will refer below to this catalyst as catalyst B.

EXAMPLE 1

This example illustrates the degradation of a polymer of the low molecular-weight polyethylene type according to the process of the invention.

Figure 1:
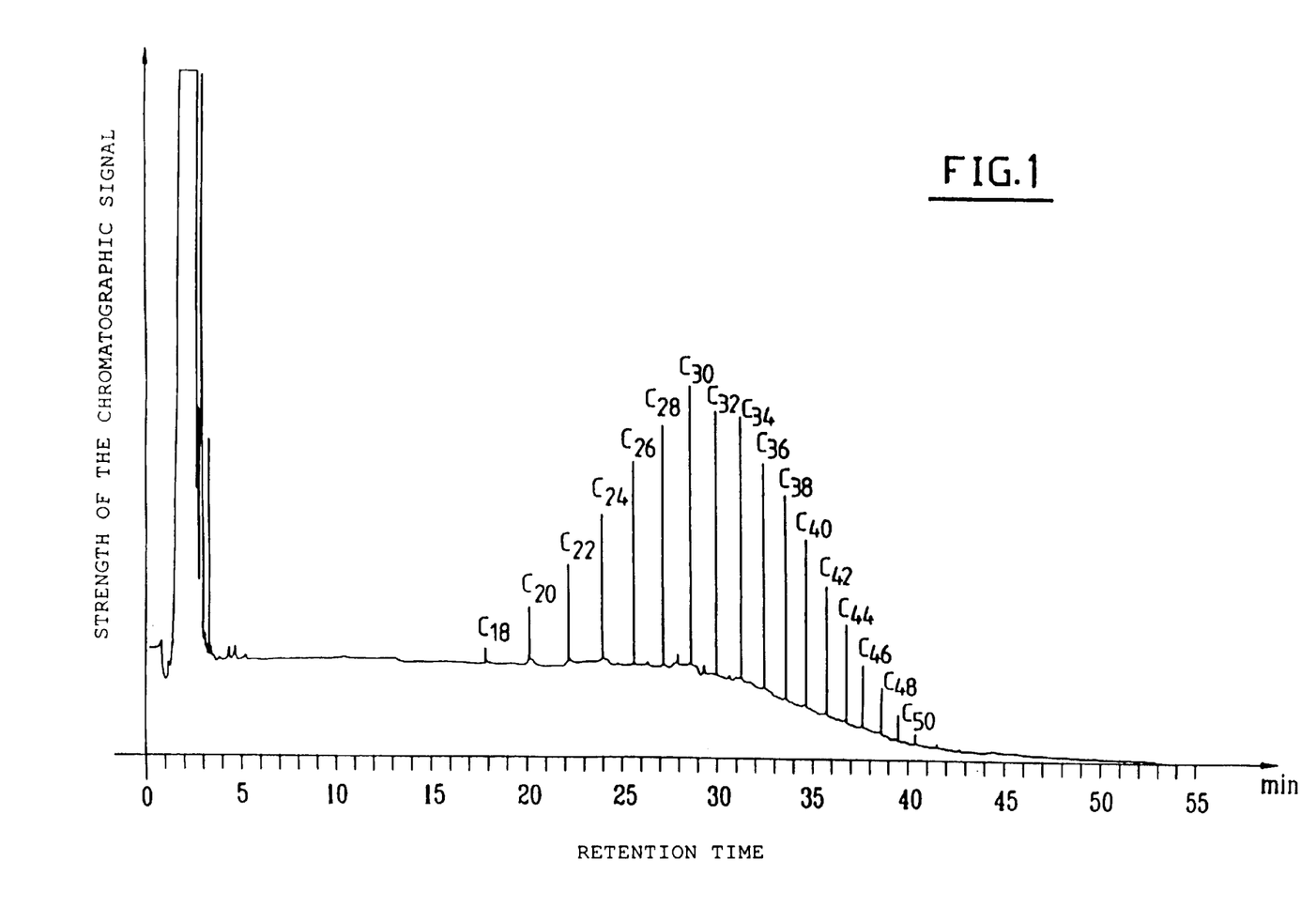
FIG. 1 is a chromatogram obtained by gas phase chromatography (GPC) of a low molecular-weight polyethylene polymer which can be degraded by the process of the invention.

This type of polyethylene includes a fairly broad distribution of molecular masses, ranging from about $C_{18}$ to $C_{60}$. The distribution of the oligomers according to the number of carbons in their chain, which is determined by gas phase chromatography, is presented in FIG. 1. The chromatogram, as well as all the other chromatograms which are presented, was produced with a temperature gradient in the oven. The temperature programme is as follows:

initial temperature 100° C., maintained for 10 min;
increase by 10° C./min to 390° C.

The temperature of the injector and the detector is 400° C.

In the chromatogram in FIG. 1, each peak corresponds to the detection of one oligomer. It appears that all the oligomers which are detected have an even number of carbon atoms, in accordance with the macromolecular structure of polyethylene.

Figure 2:
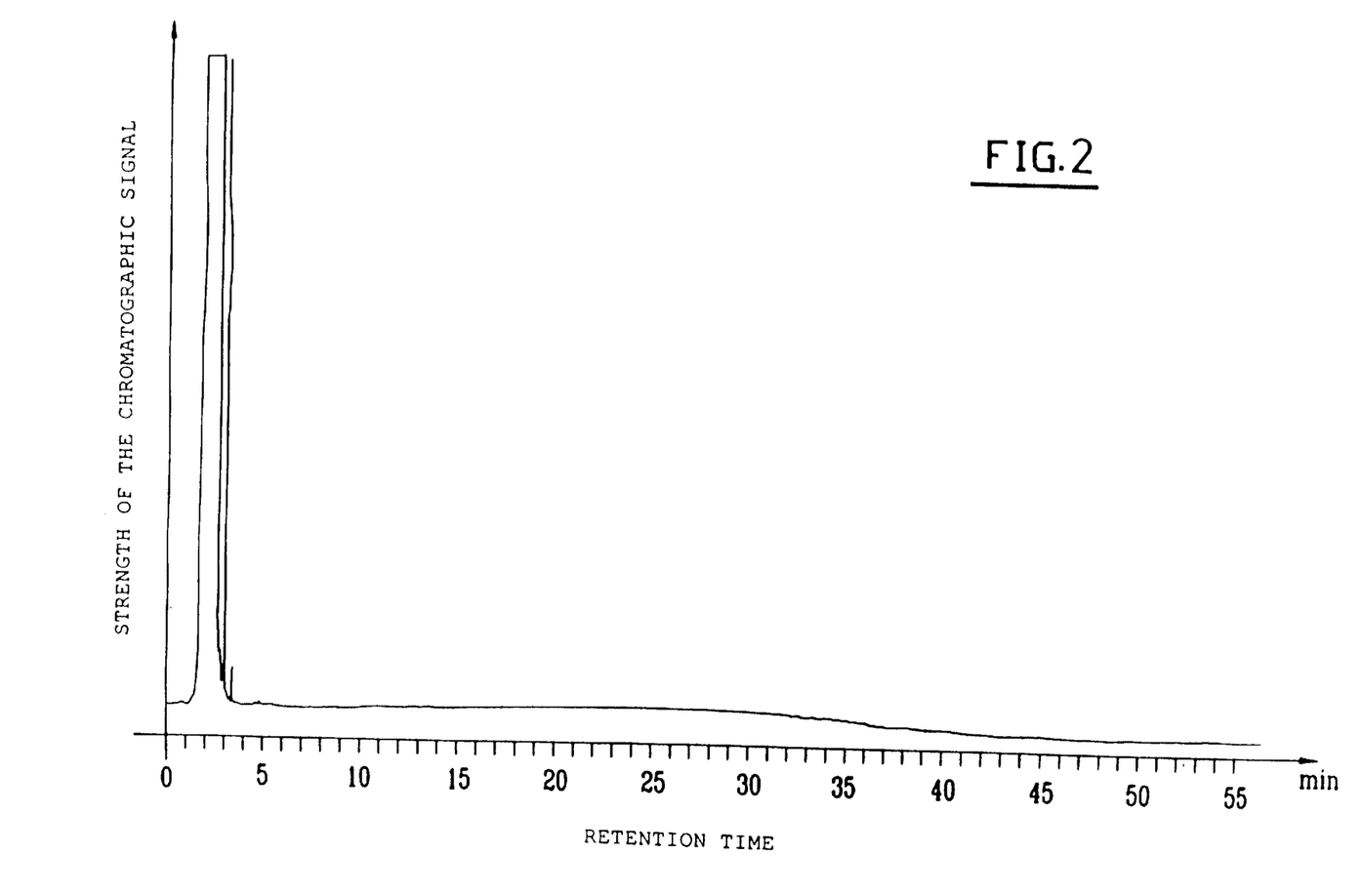
FIGS. 2 to 5 are chromatograms, obtained by GPC, of the product of the degradation of the aforementioned low molecular-weight polyethylene by the process of the invention, with a first catalyst, after variable treatment times.

In a typical experiment, 70 mg of catalyst A were introduced into a glass reactor having a volume of 482 ml. The corresponding quantity of zirconium is 0.023 mmol. 115 mg of polyethylene were then introduced into the reactor under an inert atmosphere. The corresponding quantity of carbon atoms in the polymer chains is $8.10^{-3}$ mol. Lastly, a hydrogen pressure of $10^5$ Pa was established in the reactor at room temperature. The corresponding quantity of hydrogen gas is $19.7·10^{-3}$ mol. The reactor was heated to 150° C. for 62 hours. The gases released were analysed by gas phase chromatography on a fused silica capillary column of the CHROMPACK $Al_2O_3$/KCl type; length 50 m*internal diameter 0.32 mm. The heavy hydrocarbons of the oligomer type were extracted from the reaction residue in the reactor using hot decalin, then analysed by GPC (capillary column of the HT5 type, 0.1 mm; 12 m*0.22 mm covered with alumina) to give the chromatogram in FIG. 2.

The results of the gas phase analysis show a conversion ratio of 94 (±5)% of the initial polyethylene into light alkanes with fewer than 9 carbon atoms. The chromatogram in FIG. 2, corresponding to the analysis of the heavy hydrocarbons of the oligomer type extracted in decalin, has no peak in the retention time range demonstrated in FIG. 1 and corresponding to the initial oligomers. There is therefore no longer any initial polyethylene or oligomers of lower molecular weight. In contrast, the presence of methane, ethane, propane, butanes, pentanes and hexanes is noted. The proportions of these various hydrocarbons will be indicated in Table 1, which collates the comparative results of application examples 1 to 4.

By way of comparison, the same reaction was carried out without catalytic metal hydride, but simply in the presence of the silica/alumina support.

70 mg of the silica/alumina used in reference example 1 were treated under the same conditions as in this reference example 1, but without introducing the zirconium complex.

The same low molecular-weight polyethylene was subjected to a treatment under hydrogen in the same conditions as those described above, while replacing catalyst A by ungrafted silica/alumina. After 62 hours of reaction, no significant quantity of products of the light alkane type, or even oligomers, could be detected.

This comparative experiment shows that the support of the catalyst is inactive in the applied conditions, and that the degradation of polyethylene is made possible in these conditions by zirconium hydride.

EXAMPLE 2

This example, as well as the two examples which follow, illustrates the fact that the nature of the reaction products can be controlled by altering the duration of the reaction.

The protocol in Example 1 was reproduced exactly, apart from the fact that the reactor was heated for only one hour.

The results of the gas phase analysis show a conversion ratio of 5% of the initial polyethylene into light alkanes lower than $C_9$.

Figure 3:
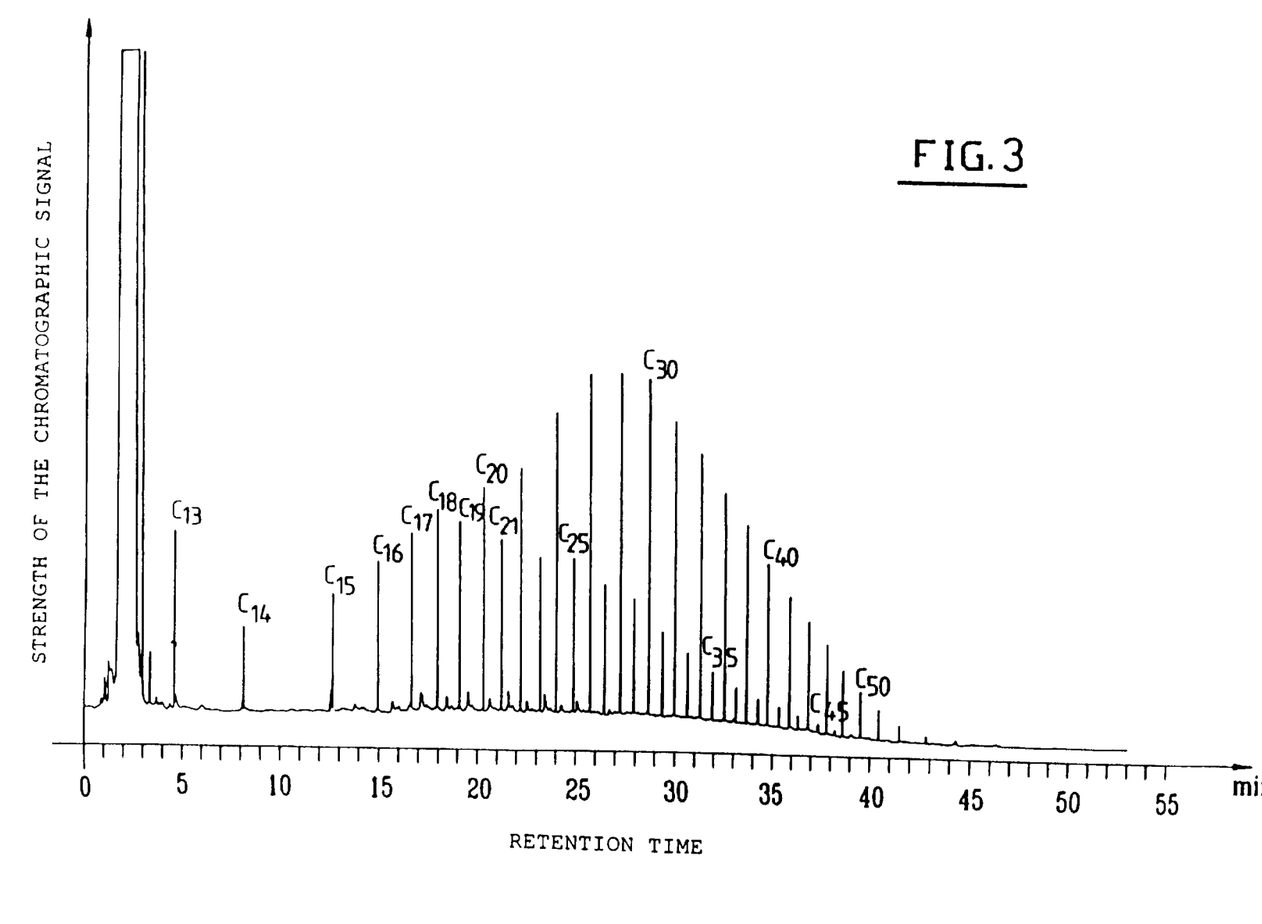

The chromatogram in FIG. 3, corresponding to the analysis of the heavy hydrocarbons of the oligomer type which were extracted in decalin, shows that the initial polyethylene has undergone deep modifications to the molecular mass distribution.

Thus, the proportion of oligomers with lower molecular weight increases in the distribution of the even oligomers, showing that the cleavage reaction takes place.

The appearance, between the peaks corresponding to the initial oligomers, of new peaks corresponding to the intermediate oligomers with an odd number of carbon atoms is furthermore noted, demonstrating that the cleavage of the carbon—carbon bonds of the initial polymer is stochastic. The distribution of the oligomers having an odd number of carbons reaches its maximum at about $C_{20}$.

Lastly, as regards the lighter hydrocarbons, the presence of detectable quantities of alkanes ranging from $C_1$ to $C_7$ is noted, in particular methane, ethane, propane, butanes, pentanes and hexanes. The proportions of these various hydrocarbons will be indicated in Table 1.

EXAMPLE 3

Like the previous one, this example illustrates the fact that the nature of the reaction products can be controlled by altering the duration of the reaction.

The protocol in Example 1 was reproduced exactly, apart from the fact that the reactor was heated for only two hours.

The results of the gas phase analysis show a conversion ratio of 25% of the initial polyethylene into light alkanes having a carbon number lower than $C_9$.

Figure 4:
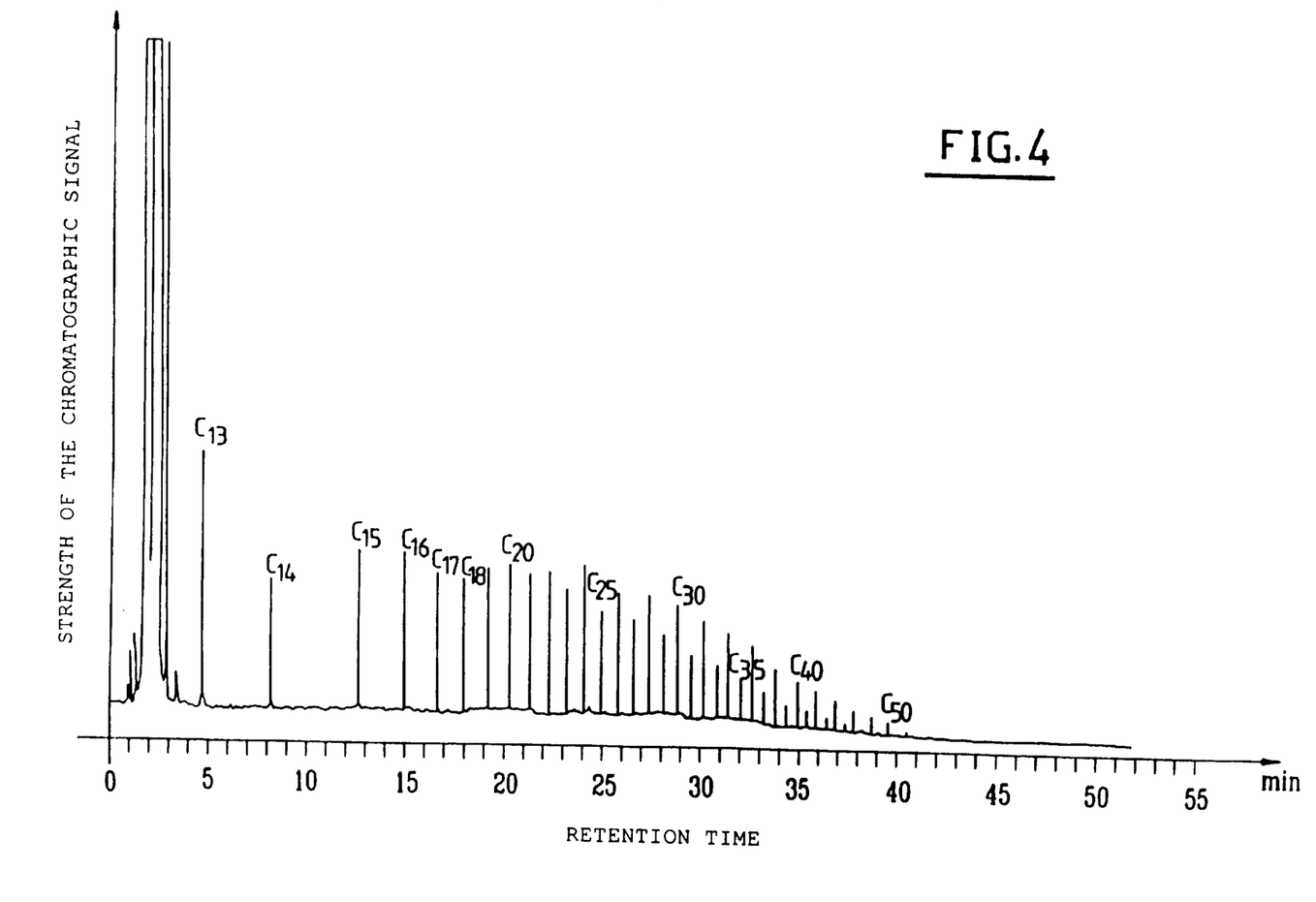

The chromatogram in FIG. 4, corresponding to the GPC analysis of the heavy hydrocarbons of the oligomer type which were extracted in decalin, shows that the initial polyethylene has undergone very deep modifications to the molecular mass distribution; in particular it is noted that oligomers having an odd number of carbons appear in quantities substantially equivalent to that of the oligomers with an even number of carbons; this demonstrates a broad distribution of oligomers with carbon number maxima at about $C_{18}$ and $C_{26}$.

Lastly, as regards the lighter hydrocarbons, detectable quantities of alkanes ranging from $C_1$ to $C_8$ are noted, as indicated in Table 1.

EXAMPLE 4

Like the previous one, this example illustrates the fact that the nature of the reaction products can be controlled by altering the duration of the reaction.

The protocol in Example 1 was reproduced exactly, apart from the fact that the reactor was heated for only five hours.

Figure 5:
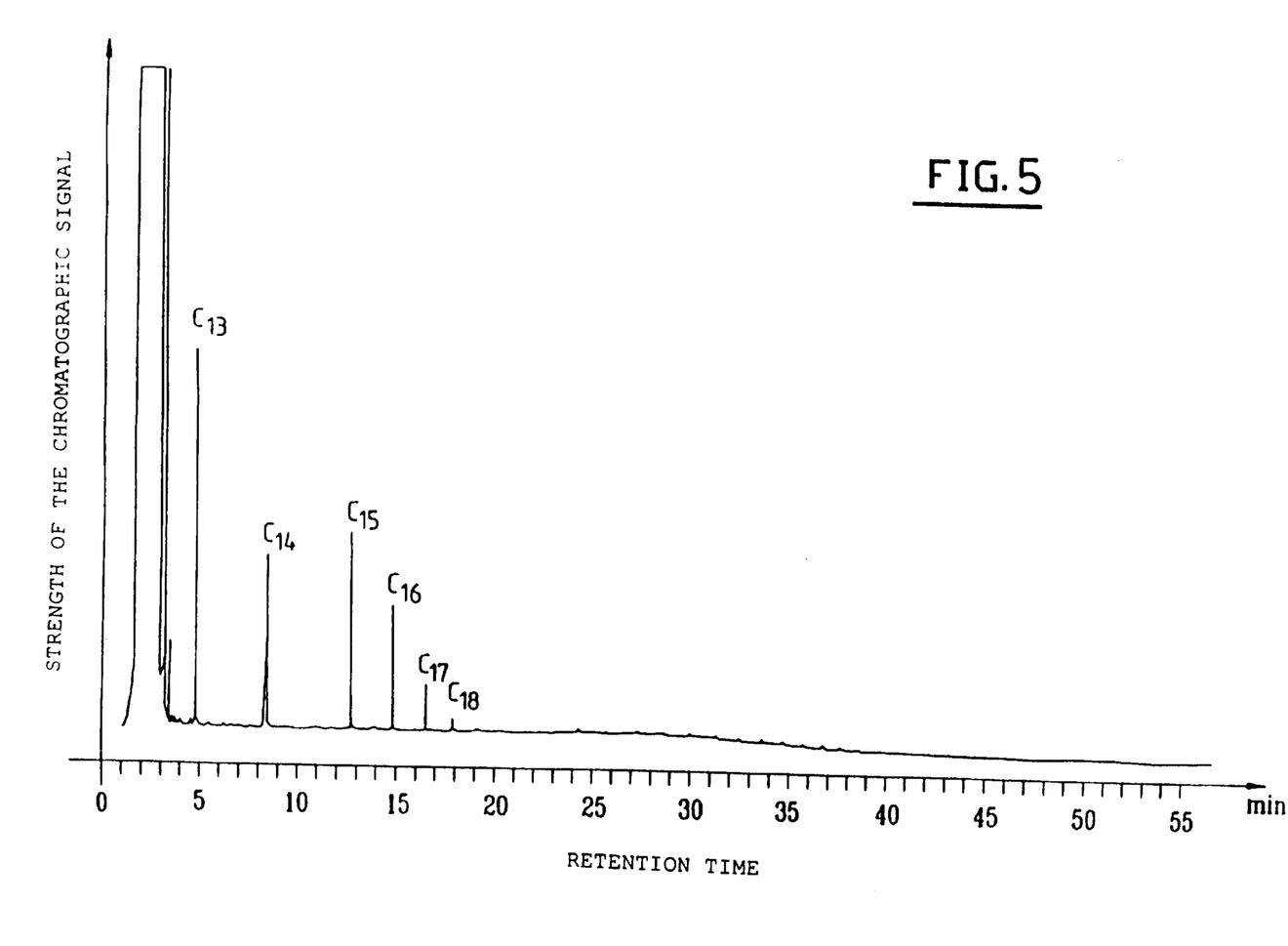

The results of the gas phase analysis show a conversion ratio of 84% of the initial polyethylene into light alkanes having a carbon number lower than $C_9$. The chromatogram in FIG. 5, corresponding to the GPC analysis of the heavy hydrocarbons of the oligomer type which were extracted in decalin, shows that the initial polyethylene has virtually disappeared. Only a hydrocarbon fraction ranging from $C_{10}$ to $C_{18}$ is left. Lastly, as regards the lighter hydrocarbons, very significant quantities of alkanes ranging from $C_1$ to $C_9$ are noted, which are indicated in Table 1 below.

Table 1 shows the effect of the reaction time on the distribution of the $C_1$ to $C_8$ hydrocarbons for the same quantity of catalyst, for the same quantity of polyethylene, for the same quantity of hydrogen and for the same temperature.

EXAMPLE 5

This example illustrates the degradation of the same polyethylene polymer, catalysed by catalyst B.

In a typical experiment, 60 mg of catalyst B were introduced into a glass reactor having a volume of 300 ml. The corresponding quantity of zirconium is 0.019 mmol. 95 mg of polyethylene were then introduced into the reactor under an inert atmosphere. The quantity of carbon atoms in the polymer chains is $6.8 \cdot 10^{-3}$ mol. Lastly, a hydrogen pressure of $8.5 \cdot 10^4$ Pa was established in the reactor. The corresponding quantity of hydrogen gas is $10.5 \cdot 10^{-3}$ mol. The reactor was then heated to 150° C. for 30 hours. The gases released were analysed by gas phase chromatography (fused silica capillary column of the CHROMPACK $Al_2O_3/KCl$ type; length 50 m*internal diameter 0.32 mm). The heavy hydrocarbons of the oligomer type were extracted using hot decalin, then analysed by GPC (capillary column of the HT5 type, 0.1 mm; length 12 m*internal diameter 0.22 mm covered with alumina) to give the chromatogram in FIG. 6.

The results of the gas phase analysis show a conversion ratio of 32% of the initial polyethylene into light alkanes lower than $C_9$, the distribution of which is indicated in Table 2 below.

Figure 6:
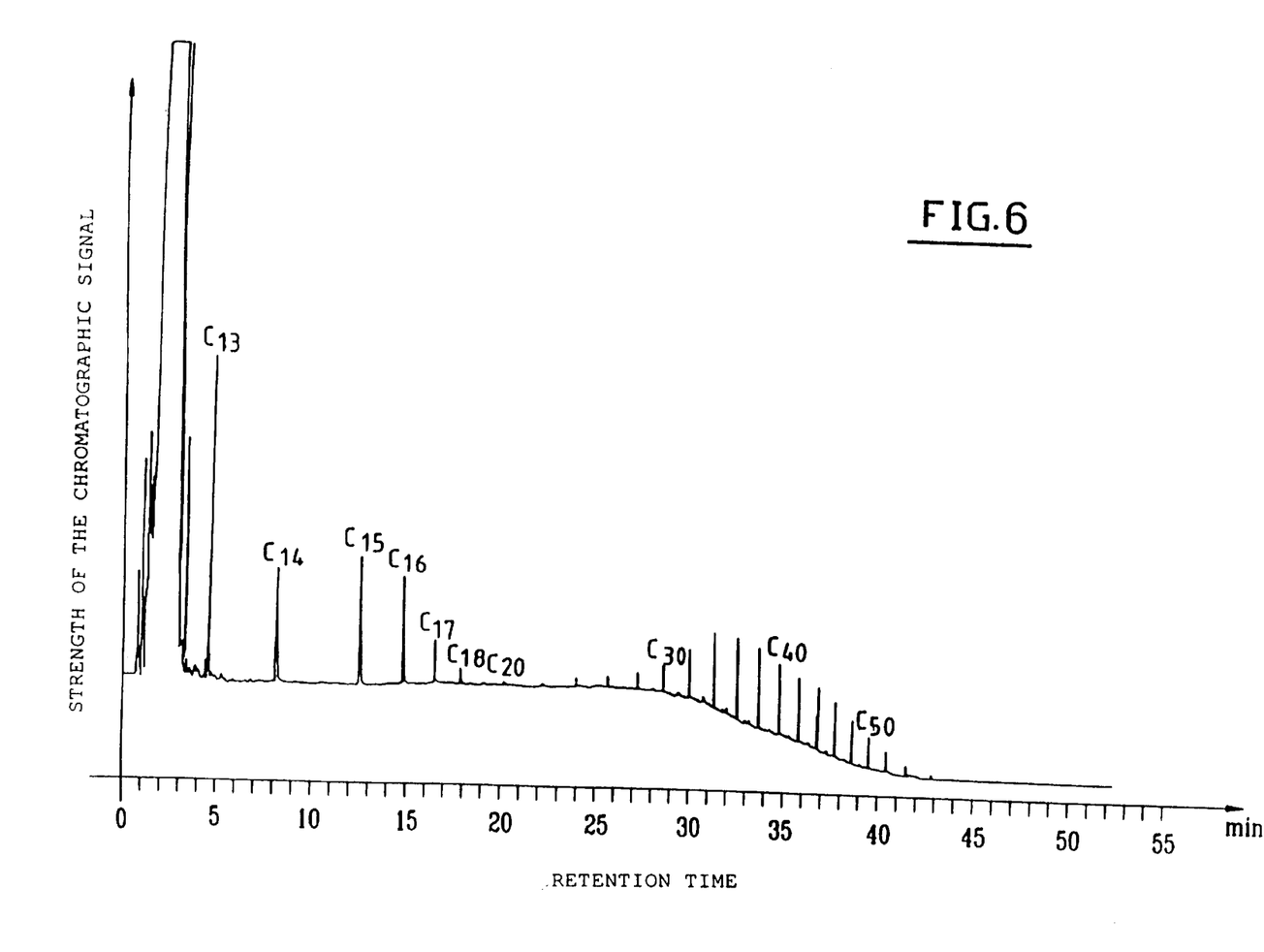
FIG. 6 is a chromatogram, obtained by GPC, of the product of the degradation of the aforementioned low molecular-weight polyethylene according to the process of the invention, with a second catalyst.

The distribution of the oligomers appearing on the chromatogram in FIG. 6, corresponding to the GPC analysis of the heavy hydrocarbons of the oligomer type which were extracted in decalin, is singularly modified, both with respect to that of the initial polymer and with respect to that of the degradation products obtained in the conditions of the previous application examples 1 to 4.

The formation of a significant fraction of hydrocarbons ranging from $C_{10}$ to $C_{18}$ is noted, while a relatively large quantity of even oligomers between $C_{30}$ and $C_{50}$ is left.

In this case, it is also confirmed that silica, pretreated as in reference example 2 without the introduction of zirconium complex, is inactive for the catalytic hydrocracking of polyethylene in the conditions which were studied.

The same comparative experiment can also be carried out with niobium oxide treated in the conditions of reference example 1, without the introduction of the zirconium complex. It is confirmed that niobium oxide treated in this way is also inactive for the catalytic hydrocracking of polyethylene in the conditions of Examples 1 to 5.

TABLE 1

| Example | Reaction time | Total conversion (mol %) | Of which conversion into: (mol %) | | | | | | | |
| --- | --- | --- | --- | --- | --- | --- | --- | --- | --- | --- |
| | | | Methane | Ethane | Propane | Butanes | Pentanes | Hexanes | Heptanes | Octanes |
| 1 | 62 | 94.13 | 5.56 | 25.47 | 25.66 | 24.31 | 12.45 | 0.67 | — | — |
| 2 | 1 | 4.92 | 0.23 | 0.99 | 0.80 | 1.03 | 1.15 | 0.47 | 0.25 | — |
| 3 | 2 | 24.94 | 0.71 | 3.98 | 3.15 | 4.13 | 4.86 | 4.29 | 2.68 | 1.15 |
| 4 | 5 | 83.80 | 64 | 12.31 | 13.41 | 17.30 | 18.74 | 12.89 | 5.25 | 1.26 |

TABLE 2

| Total conver-sion (mol %) | Of which conversion into: (mol %) | | | | | | | |
|---|---|---|---|---|---|---|---|---|
| | Meth-ane | Eth-ane | Pro-pane | But-anes | Pen-tanes | Hex-anes | Hep-tanes | Oc-tanes |
| 31.88 | 1.71 | 4.61 | 5.18 | 6.70 | 6.94 | 4.24 | 2.29 | — |

EXAMPLE 6

This example illustrates the application of the catalytic process in liquid phase, using an inert solvent in which the polymer and the catalyst are in suspension.

In a typical experiment, 70 mg of catalyst A were introduced into a glass reactor having a volume of 300 ml. The corresponding quantity of zirconium is 0.023 mmol. 100 mg of polyethylene identical to that used in the previous examples were then introduced into the reactor under an inert atmosphere. The quantity of carbon in the polymer chains is $7.4 \cdot 10^{-3}$ mol. 4 ml of decalin, dried beforehand, were then added under an inert atmosphere. Lastly, a hydrogen pressure of $6.5 \cdot 10^4$ Pa was established in the reactor. The corresponding quantity of hydrogen gas is $8.07 \cdot 10^{-3}$ mol. The reactor was then heated to 150° C. for 30 hours. The gases released were analysed by gas phase chromatography (fused silica capillary column of the CHROMPACK $Al_2O_3$/KCl type; 50 m*0.32 mm) and the heavy hydrocarbons of the oligomer type were extracted using hot decalin, then analysed by GPC (capillary column of the HT5 type, 0.1 mm; 12 m*0.22 mm covered with alumina) to give the chromatogram in FIG. 7.

Figure 7:
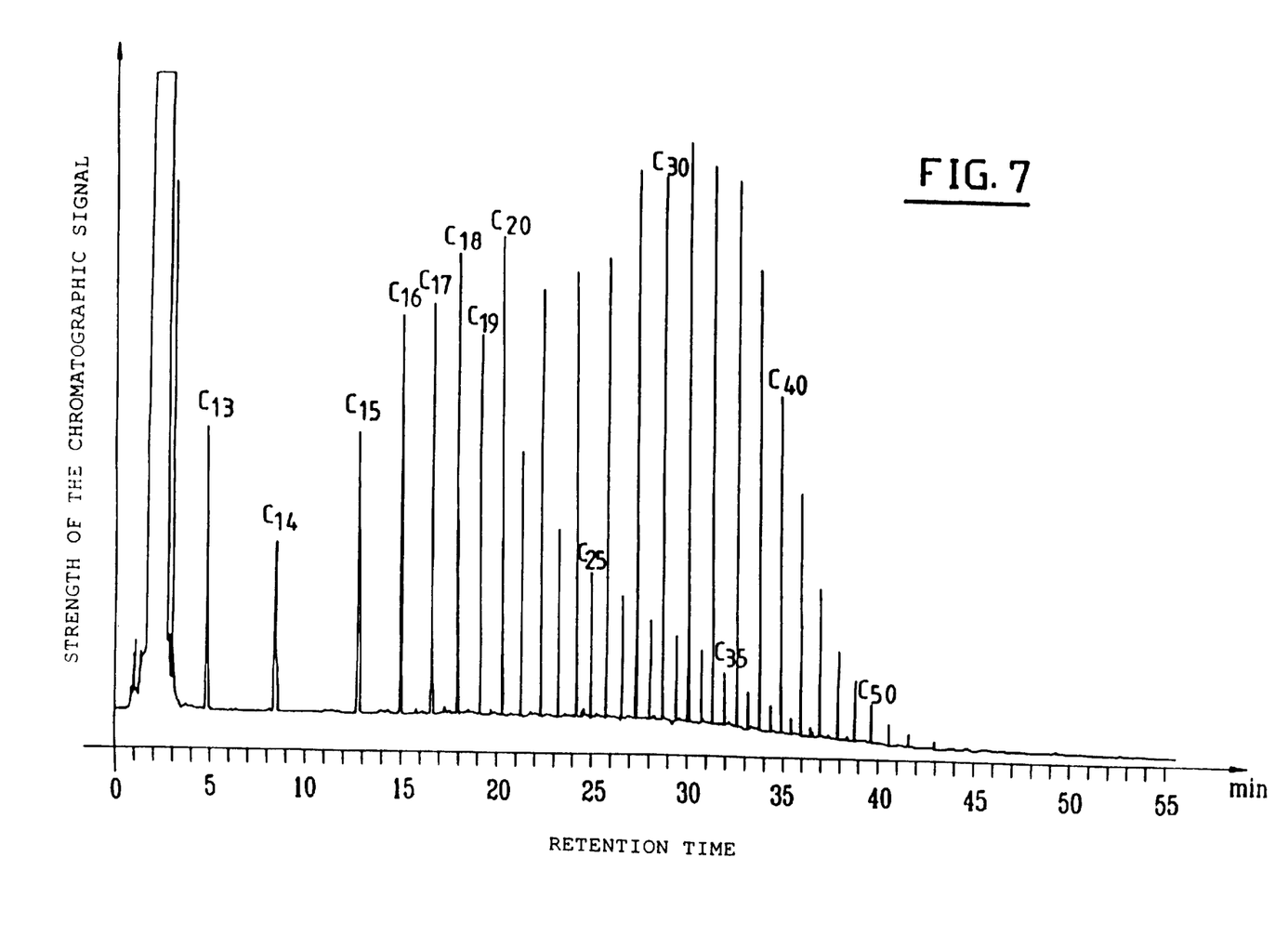
FIG. 7 is a chromatogram, obtained by GPC, of the product of the degradation of an aforementioned low molecular-weight polyethylene according to the process of the invention, in a solvent medium.

The analysis of the heavy hydrocarbons of the oligomer type which were extracted in decalin shows that the initial polyethylene has undergone deep modifications in the molecular mass distribution, as appears clearly in FIG. 7. A shift in the oligomer distribution is observed towards low masses. Furthermore, the appearance of oligomers having an odd number of carbons is noted, as before demonstrating that the cleavage of the carbon—carbon bonds of the initial polymer is stochastic. The oligomer distribution is consequently broader, with carbon number maxima at about $C_{20}$ and $C_{32}$. The analysis of the gas phase indicates the presence of detectable quantities of alkanes ranging from $C_1$ to $C_7$.

It is confirmed that, when they are pretreated as in the reference examples without introducing zirconium complex, both silica/alumina and silica or niobium oxide are not active for the hydrocracking of polyethylene in these conditions.

EXAMPLE 7

This example illustrates the application of the catalytic process for converting a high molecular-weight polypropylene into light alkanes and oligomers of lower molecular weight.

In a typical experiment, 70 mg of catalyst A were introduced into a glass reactor having a volume of 300 ml. The corresponding quantity of zirconium is 0.023 mmol. 136 mg of polypropylene having an average molecular mass of 250,000 were then introduced into the reactor under an inert atmosphere. The quantity of carbon atoms in the polymer chains is $9.71 \cdot 10^{-3}$ mol. Lastly, a hydrogen pressure of 105 Pa was established in the reactor. The corresponding quantity of hydrogen gas is $12.75 \cdot 10^{-3}$ mol. The reactor was then heated to 200° C. for 15 hours.

The gases released were analysed by gas phase chromatography (fused silica capillary column of the CHROMPACK $Al_2O_3$/KCl type; 50 m*0.32 mm).

The results of the analysis of the gas phase show a conversion ratio of 40% of the initial polypropylene into light alkanes lower than $C_8$, particularly into methane, ethane, propane, butanes, pentanes, hexanes and heptanes, as is indicated in Table 3 below.

It is confirmed that, when they are pretreated as in the reference examples without introducing zirconium complex, both silica/alumina and silica or niobium oxide are not active for the hydrocracking of polypropylene in these conditions.

TABLE 3

| Total conver-sion (%) | Of which conversion into % | | | | | | | |
|---|---|---|---|---|---|---|---|---|
| | Meth-ane | Eth-ane | Pro-pane | But-anes | Pen-tanes | Hex-anes | Hep-tanes | Oc-tanes |
| 40.43 | 11.66 | 5.69 | 6.24 | 7.26 | 6.01 | 2.81 | 0.77 | — |

EXAMPLE 8

This example illustrates the application of the catalytic process for converting a high molecular-weight polystyrene into alkanes and light aromatics (lower than $C_6$) and oligomers of lower molecular weight.

In a typical experiment, 75 mg of catalyst A were introduced into a glass reactor having a volume of 482 ml. The corresponding quantity of zirconium is 0.024 mmol. 127 mg of polystyrene (in the form of balls, but ground beforehand before use) having an average molecular mass of 45,000 were then introduced into the reactor under an inert atmosphere. The number of mols of polystyrene unit —[CH(Ph)$CH_2$]— in the polymer chain is $1.22 \cdot 10^{-3}$ mol. Lastly, a hydrogen pressure of $10^5$ Pa was established in the reactor. The corresponding quantity of hydrogen gas is $19.7 \cdot 10^{-3}$ mol. The reactor was then heated to 150° C. for 15 hours.

The gases released were analysed by gas phase chromatography (fused silica capillary column of the CHROMPACK $Al_2O_3$/KCl type; 50 m*0.32 mm) coupled with mass spectrometry.

The results of the qualitative analysis of the gas phase indicate that the initial polystyrene has been degraded, principally into benzene.

Small but detectable quantities of light alkanes whose number of carbons is less than 6, particularly methane, ethane, propanes, butanes, pentanes and hexanes were also observed.

It is confirmed that, when they are pretreated as in the reference examples without introducing zirconium complex, both silica/alumina and silica or niobium oxide are not active for the hydrocracking of polypropylene in these conditions.

EXAMPLE 9

This example illustrates the preparation of a catalyst of the zirconium alkyl complex type supported on silica/alumina, and its use in the degradation of a polymer of the low molecular-weight polyethylene type according to the process of the invention.

After having been calcined under a continuous flow of oxygen at 500° C. for 10 hours, 5 g of silica/alumina (specific surface=380 m²/g) containing 25% of aluminium were introduced into a glass reactor and treated under strong vacuum (1.33·10⁻² Pa) at 500° C. overnight.

After this treatment, 617 mg of ZrNp₄ (Np=neopentyl) were sublimed at 70° C. onto the inorganic support. The reaction between the zirconium alkyl complex and the inorganic support takes place at 25° C. and leads to the formation of a majority surface species which satisfies the formula ($\equiv$SiO)$_\alpha$ZrNp$_\beta$ and to the release, in the present case, of neopentane.

The initial ZrNp₄ complex which may not have reacted is separated at 70° C. by setting up a strong vacuum.

After this treatment, the inorganic support, namely silica/alumina, has a zirconium content of 3%.

In a typical hydrocracking experiment, 70 mg of this catalyst were introduced into a glass reactor having a volume of 482 ml. The corresponding quantity of zirconium is 0.023 mmol. 115 mg of polyethylene were then introduced into the reactor under an inert atmosphere. The quantity of carbon atoms in the corresponding polymer chains is $8·10^{-3}$ mol. Lastly, a hydrogen pressure of $10^5$ Pa was established in the reactor at room temperature. The corresponding quantity of hydrogen gas is $19.7·10^{-3}$ mol. The reactor was then heated to 150° C. for 62 hours.

The results of the analysis of the gas phase show a conversion ratio of 94 (±5)% of the initial polyethylene into light alkanes having fewer than 9 carbon atoms. Similarly, the analysis of the heavy hydrocarbons of the oligomer type which were extracted in decalin has no peak in the retention time range demonstrated in FIG. 1 and corresponding to the initial oligomers.

The results are identical to those obtained with catalyst A, which confirms that the transfer of hydrogen to the polymer is indeed carried out, by the supported alkylzirconium catalyst, via a transient surface hydride complex, in the conditions of the degradation reaction.

EXAMPLE 10

This example illustrates the application of the catalytic process for converting a wax (hydrocarbon fraction) into light alkanes and oligomers of lower molecular weight (diesel).

In a typical experiment, 70 mg of catalyst A were introduced into a glass reactor having a volume of 300 ml. The corresponding quantity of zirconium is 0.023 mmol. 500 mg of a wax derived from a Fischer-Tropsch in $C_{12}$ to $C_{15}$ were then introduced into the reactor under an inert atmosphere. The quantity of carbon atoms in the wax chains is $35.71·10^{-3}$ mol. Lastly, a hydrogen pressure of 105 Pa was established in the reactor. The corresponding quantity of hydrogen gas is $12.75·10^{-3}$ mol. The reactor was then heated to 200° C. for 20 hours and the gases released were analysed by gas phase chromatography or liquid phase chromatography.

After 2 hours of reaction, the formation of a very important fraction of hydrocarbon in $C_{12}$ to $C_{20}$ (corresponding to about 50% of conversion) is observed. After 20 hours of reaction, a much more important quantity of wax is converted and very light alkanes, from $C_1$ to $C_6$ are obtained as indicated in Table 4 below.

TABLE 4

| Example | Timed reaction (hours) | Total conversion into % | of which conversion into % | | | | | |
|---|---|---|---|---|---|---|---|---|
| | | | $C_1$ | $C_2$ | $C_3$ | $C_4$ | $C_5$ | $C_6$ |
| 10 | 20 | 100 | 20 | 39.7 | 15.8 | 10.2 | 10.6 | 3.7 |

What is claimed is:

1. A process for the conversion of a material selected from a wax, a polymer and an oligomer, said polymer and said oligomer deriving from an ethylenically unsaturated monomer, into alkanes or a hydrocarbon fraction or an oligomer fraction of the lower variety by controlled hydrocracking, comprising the following steps:
   bringing the wax or polymer or oligomer into the presence of a catalyst which is either a metal hydride supported on an inorganic support or an organometallic complex supported on an inorganic support, said inorganic support being a divided solid comprising a metal oxide or a mixture of metal oxides, said complex including at least one hydrocarbon ligand, and optionally at least one hydride ligand, then
   reacting this mixture with hydrogen, thus catalytically hydrocracking said polymer or oligomer,
   and recovering said alkanes hydrocarbon fraction or oligomer fraction of the lower variety.

2. A process according to claim 1, wherein the metal in the organometallic complex or metal hydride is a transition metal selected from the group consisting of the metals of groups IIIb, IVb, Vb and VIb of the Periodic Table, including lanthanides and actinides.

3. A process according to claim 1, wherein the metal in the organometallic complex or metal hydride is a transition metal selected from the group consisting of titanium, zirconium, hafnium, vanadium, niobium, tantalum, scandium, yttrium and lanthanum.

4. A process according to claim 1, wherein the support is selected from the group consisting of silica/alumina, silica, alumina, niobium oxide and zeolites.

5. A process according to claim 1, wherein the catalyst comprises a transition metal hydride complex supported on a divided metal oxide.

6. A process according to claim 1, wherein said catalyst is an organometallic complex in which said hydrocarbon ligand is selected from the group of ligands consisting of alkyl, carbene, carbyne, carbonyl, aryl, acyl, arene and diene which is optionally substituted.

7. A process according to claim 1, wherein said catalyst is an organometallic complex including at least one alkyl ligand.

8. A process according to claim 1, wherein said catalyst is an organometallic complex including at least one hydride ligand and prepared by
   (i) reacting said support with a compound of the metal of formula (1), (2) or (3)

$$MH_xR_y \quad (1)$$

$$M(O)_nH_pR_q \quad (2)$$

$$M(OR')_nH_pR_q \quad (3)$$

in which M is the metal,
H is a hydride ion, x is an integer that may be zero,
R is a hydrocarbon ligand,
y is an on-zero integer,
R' is an alkyl group,
n and q are non-zero integers,
p is an integer that may be zero, and (ii) subjecting the product of step (i) to hydrogenation.

9. A process according to claim 1, wherein said catalyst is an organometallic complex including at least one hydride ligand and prepared by (i) reacting said support with a compound of the metal of formula (1), (2) or (3)

$$MH_xR_y \qquad (1)$$

$$M(O)_nH_pR_q \qquad (2)$$

$$M(OR')_nH_pR_q \qquad (3)$$

in which M is the metal,
H is a hydride ion,
x is an integer that may be zero,
R is a hydrocarbon ligand,
y is a non-zero integer,
R' is an alkyl group,
n and q are non-zero integers,
p is an integer that may be zero, and (ii) subjecting the product of step (i) to hydrogenation at a temperature of from 50 to 250° C.

10. A process according to claim 1, wherein the wax is a saturated or optionally an olefinic hydrocarbon in $C_{12}$ to $C_{50}$.

11. A process according to claim 1, wherein the wax derives from Fischer and Tropsch's synthesis.

12. A process according to claim 1, wherein said polymer or oligomer has a carbon-based chain comprising at least 10 carbon atoms.

13. A process according to claim 1, wherein said polymer or oligomer is a homopolymer, a copolymer or a mixture of polymers derived from at least one of a) monomer selected from olefinic monomers having a single ethylenic unsaturation, and b) monomers having a plurality of ethylenic unsaturations.

14. A process according to claim 1, wherein the hydrocarbon skeleton of the said polymer is a saturated polyolefin.

15. A process according to claim 1, wherein the hydrocarbon skeleton of the polymer is unsaturated, and the polymer is a copolymer with at least one monomer having a single ethylenic unsaturation and with at least one monomer having a plurality of ethylenic unsaturations.

16. A process according to claim 1, wherein the said catalytic hydrocracking is carried out at a temperature of from 25 to 300° C.

17. A process according to claim 1, wherein the catalytic hydrocracking is carried out under a hydrogen pressure of from $10^3$ to $5.10^7$ Pa.

18. A process according to claim 1, wherein the duration of the catalytic hydrocracking is from 30 min to 150 h.

19. A process according to claim 1, wherein the catalytic hydrocracking is carried out in a liquid medium comprising a solvent.

20. A process according to claim 1, wherein the catalytic hydrocracking is carried out in a liquid medium comprising a solvent selected from cyclic alkanes.

21. A process according to claim 1, wherein the catalytic hydrocracking is carried out in the absence of solvent.

22. A process according to claim 1, wherein the process is carried out during the formation of the polymer or oligomer.

23. A process according to claim 1, wherein the process is carried out during the shaping of the polymer or oligomer.

* * * * *